(12) United States Patent
Papazoglou

(10) Patent No.: US 7,785,505 B2
(45) Date of Patent: Aug. 31, 2010

(54) METHODS FOR USE OF FLUORESCENT NANOPARTICLES TO DETERMINE FREE VOLUME AND TO DETECT AND DELIVER MATERIALS TO REPAIR CRACKS IN POLYMERS AND POLYMER COMPOSITES

(75) Inventor: Elisabeth S. Papazoglou, Yardley, PA (US)

(73) Assignee: Drexel University, Philadelphia, PA (US)

( * ) Notice: Subject to any disclaimer, the term of this patent is extended or adjusted under 35 U.S.C. 154(b) by 876 days.

(21) Appl. No.: 11/587,324

(22) PCT Filed: Apr. 26, 2005

(86) PCT No.: PCT/US2005/014214

§ 371 (c)(1),
(2), (4) Date: Feb. 7, 2007

(87) PCT Pub. No.: WO2005/106462

PCT Pub. Date: Nov. 10, 2005

(65) Prior Publication Data

US 2007/0178305 A1      Aug. 2, 2007

Related U.S. Application Data

(60) Provisional application No. 60/565,315, filed on Apr. 26, 2004, provisional application No. 60/565,577, filed on Apr. 27, 2004.

(51) Int. Cl.
  *B29C 45/76* (2006.01)

(52) U.S. Cl. ................................. 264/40.1; 977/902
(58) Field of Classification Search ................ 427/8; 977/902, 963; 264/21, 40.1
See application file for complete search history.

(56) References Cited

U.S. PATENT DOCUMENTS

| 2,498,592 | A | * | 2/1950 | Switzer et al. ............... 428/219 |
| 2,635,329 | A | * | 4/1953 | De Forest et al. ....... 29/890.141 |
| 5,519,211 | A | | 5/1996 | Bur et al. ................ 250/227.19 |
| 5,770,155 | A | | 6/1998 | Dunphy et al. ........... 422/82.05 |
| 5,922,537 | A | | 7/1999 | Ewart et al. .................... 435/6 |
| H1843 | H | | 3/2000 | Bur et al. .................. 250/458.1 |
| 6,149,868 | A | | 11/2000 | Natan et al. ............... 422/82.05 |
| 6,268,222 | B1 | | 7/2001 | Chandler et al. ............. 436/523 |

* cited by examiner

Primary Examiner—Glenn Caldarola
Assistant Examiner—Randy Boyer
(74) Attorney, Agent, or Firm—Woodcock Washburn, LLP

(57) ABSTRACT

Methods for use of functionalized fluorescent nanoparticles in the non-destructive, direct and dynamic determination of free volume and glass transition changes and mechanical property changes of polymers and polymer composites are provided. Also provided are methods for use of functionalized fluorescent nanoparticles in tracking changes occurring in an individual component or components of a polymer composite. Methods for use of functionalized fluorescent nanoparticles in the quantitation and dynamic monitoring of crack propagation and fatigue of polymers and/or polymer composites and in the delivery of repair agents such as adhesives and/or cross-linking agents to cracks of polymers and polymer composites are provided.

11 Claims, No Drawings

METHODS FOR USE OF FLUORESCENT NANOPARTICLES TO DETERMINE FREE VOLUME AND TO DETECT AND DELIVER MATERIALS TO REPAIR CRACKS IN POLYMERS AND POLYMER COMPOSITES

INTRODUCTION

This patent application claims the benefit of priority from U.S. Provisional Application Ser. No. 60/565,315 filed Apr. 26, 2004 and U.S. Patent Application Ser. No. 60/565,577 filed Apr. 27, 2004, each of which are herein incorporated by reference in their entirety.

BACKGROUND OF THE INVENTION

The concept of free volume available in a polymer or polymer composite has been a theoretical "construct" that enables very accurate calculation of volumetric properties of polymers and polymer composites, as temperature, pressure and mixture composition change.

However, positron annihilation experiments, requiring specialized expensive equipment, provide only an indirect free volume approximation.

In materials development, electron microscopy is currently in use. However, this process is destructive, requiring dismantling and/or removal of a sample from its environment for testing.

Thus, methods are needed to provide a non-destructive independent measurement of free volume and its change through the glass transition temperature. The ability to measure changes in free volume obtained in a continuous fashion and/or through dynamic experiments also opens new possibilities in the materials and composites and biomaterials fields.

Also needed are methods for assessing crack propagation and fatigue in polymers and polymer composites and means for repairing such cracks.

Polymers and polymer composites in use today suffer from degradation/deterioration of mechanical properties. In polymer and polymer composite structures this degradation and deterioration can lead to catastrophic failure as damage accumulates to a critical point.

Crack propagation, as a damage acceleration mechanism is a model used to follow theoretically through destructive testing of selected samples the actual damage process occurring in the field.

Ultrasound can be used to visualize damage. However, results are difficult to interpret and are generally not quantitative.

The concept of self-healing materials for repair of such cracks in polymers and polymer composites has been proposed and was demonstrated in 2001 using a polyurethane composite. This composite comprised a cross linker which was released in the damaged polymer and repaired a portion of the damage.

Currently fluorescent nanoparticles referred to as quantum dots are used as replacements for fluorescent dyes in biological and medicinal immunoassays in biology.

SUMMARY OF THE INVENTION

In the present invention, methods are provided for use of fluorescent nanoparticles in dynamic monitoring of changes in free volume of a polymer or polymer composite. It has now been found that the diffusion and/or concentration profile of functionalized fluorescent nanoparticles through a polymer matrix or polymer composite matrix provide a measurement of free volume. Further, in a polymer or polymer composite under stress, the concentration profile of the functionalized fluorescent nanoparticles can reveal nanoscopic changes occurring in the polymer or polymer composite and influencing mechanical properties of the polymer or polymer composite.

Further, the present invention provides a method for tracking changes in different components of a polymer composite using functionalized fluorescent nanoparticles that can follow targeted components in the polymer composite matrix.

The present invention also provides methods for use of functionalized fluorescent nanoparticles in the quantitation and dynamic monitoring of crack propagation and fatigue of polymers and/or polymer composites.

In addition, the present invention provides methods for delivery of repair agents, adhesives and/or cross-linking agents to repair cracks in polymers and polymer composites via attachment to the functionalized fluorescent nanoparticles.

DETAILED DESCRIPTION OF THE INVENTION

The change of volumetric and mechanical properties of polymers and polymer composites is very important, but cannot be non-destructively followed by currently available methods. Moreover, concepts such as free volume and reptation volume remain theoretical constructs, calculated from changes in volume or elastic constants. Also important is assessing the structural integrity of polymers and polymer composites. A loss in structural integrity resulting from cracks in the polymer or polymer composite can result in catastrophic failures, which can be hard to predict or anticipate. This is true across various technologies ranging from, but not limited to the aerospace industry (large complicated structures) to prosthetic devices (orthopedic, dental). In all such technologies, post-failure evaluations are not always useful because they only capture a final state, without knowledge of the dynamics and events that led to the final failure.

Several stages of crack propagation in polymers and polymer composites are believed to occur. These include initiation, arrest, acceleration and total failure.

The present invention relates to the use of functionalized fluorescent nanoparticles, which maintain their ability to fluoresce for a very long time, to directly measure free volume of a polymer or polymer composite. Further, using these functionalized fluorescent nanoparticles, the distribution of free volume can be monitored as a function of temperature, pressure and stresses on the material in question. Fluorescence intensity and optical measurements suffice to obtain the desired properties. Ability to measure while the material is in its "in use" environment" renders this technology unique and exciting. Further, the fluorescent nanoparticles used in the present invention, also commonly referred to as Quantum Dots or Q dots, can be used to non-destructively, directly and dynamically determine glass transition changes and mechanical property changes as the material is being used. The functionalized fluorescent nanoparticles can also be used in methods for tracking changes in different components of a polymer composite. In these methods of the present invention, functionalized fluorescent nanoparticles that can follow targeted components in the polymer matrix are used.

Use of these functionalized fluorescent nanoparticles differs from prior art methods in the size of the delivery, its targeted mode, and the ability to see what is happening.

By "functionalized" as used herein it is meant that the fluorescent nanoparticle or Quantum dot is attached, preferably covalently, to a molecule that recognizes and attaches to a selected molecular component of the polymer or polymer composite. Thus, for example, in a glass filled polymer composite, the glass fibers can be followed and how their changes affect free volume and mechanical properties monitored, with, for example a red color quantum dot functionalized to attach to the glass fiber, while another green color quantum dot functionalized to attach to a polymer component can be used to track changes in the polymer component of the matrix composite. Additional examples comprise attachment of a functionality which recognizes alcohol moieties or amide moieties to fluorescent nanoparticles to monitor exposure of such moieties upon damage or aging of the polymer or polymer composite.

When constructing a concentration profile, in accordance with methodologies described herein, wherein probing of the polymer or polymer composite structure at a certain depth is required, it may be preferable to use quantum dots that emit in the near infrared region of light. Emission at various depths can then be followed using a spectrophotometer.

These functionalized fluorescent nanoparticles can also be used to detect, monitor and/or quantify crack propagation in polymers and polymer composites in the various stages and to deliver repair agents including but not limited to adhesives and cross linking agents to the cracks. In these embodiments, the fluorescent nanoparticle is functionalized with a molecule that recognizes a moiety at the damaged crack site.

Thus, the present invention also provides methods for use of these functionalized fluorescent nanoparticles that maintain their ability to fluoresce for a very long time to quantitatively follow and optically image crack propagation and damage accumulation. Fluorescence intensity and optical imaging suffice to obtain the desired behavior. Ability to measure and visualize while the material is in its "in use" environment" renders this technology unique and exciting.

This method of the present invention using fluorescent nanoparticles allows for quantitation and dynamic monitoring of crack damage in polymers and polymer composites. Further, use of these fluorescent nanoparticles in the present invention provides for nondestructive dynamic, independent measurement of crack propagation and damage accumulation.

Ultrasound can be used as an adjunct to the methodologies of the present invention to deliver the fluorescent nanoparticles.

Further, as important as seeing and understanding the damage, the present invention is also useful in delivery of key molecules to the damaged site for repair thereof in a self-repair, self-healing mode. Nanoparticles, functionalized to target sites of damage and/or cracks, fluoresce, thereby showing where repair is needed. Further, the fluorescent nanoparticles can be modified to carry a repair agent such as an adhesive or cross-linking agent. This means that if a polymer chain is broken and hence catastrophic molecular weight degradation will occur, a targeted nanoparticle can deliver a repair agent, for example a cross linking agent, at that site providing a link to the broken chain.

Various means for contacting a polymer or polymer composite with the functionalized fluorescent nanoparticles to carry out the methodologies of the present invention are available. For example, in one embodiment, a solution comprising the functionalized fluorescent nanoparticles is sprayed on a polymer or polymer composite surface. In this embodiment, the nanoparticles, if, for example they are functionalized to attach to damage sites, will then diffuse through cracks in the polymer or polymer composite to the site of damage. Fluorescence can then be seen even at subsurface layers with digital photography, special filters, and/or cross polarizers that provide for examination of subsurface events.

In another embodiment, the functionalized fluorescent nanoparticles can be incorporated into the original polymer composite. In this embodiment, wherein the quantum dots are part of the original composition or structure, images can be taken at various times and a profile of the compositions followed to determine if and when changes in the free volume and/or structural integrity of the polymer composite occur.

The methods of the present invention thus provide a means to follow optically the velocity of crack propagation and identify the events that can decelerate or accelerate crack propagation. Methods of the present invention are useful at a fundamental level to better our understanding of the damage mechanism in a material. Methods of the present invention are also useful as a quality control tool. For example, methods can be used in determining damage to an airplane wing, determining differences in damage among airplanes of the same age, and/or determining differences in damage of different airplane designs. Alternatively, the methods can be used to assess key parameters leading to failure of prosthetic devices as well as key parameters that prevent or decrease damage. In dental materials and prosthetic orthopedic devices, this technology also provides a new means of following damage. Thus, the methods described herein are useful in various industries including, but not limited to the aerospace industry, for example in the manufacture of planes and space vehicles, the automotive industry, composite part manufacturing, polymer and polymer composite adhesive manufacturing, and manufacturer of prosthetic devices including but not limited to orthopedic devices and dental materials.

As will be understood by those of skill in the art upon reading this disclosure, the above-described uses merely serve as a few examples of the wide multitude of uses for these methodologies of the present invention.

What is claimed is:

1. A method for dynamically monitoring changes in free volume of a polymer or polymer composite as a function of temperature, pressure or stress on the polymer or polymer composite comprising:
    (a) applying a solution of functionalized fluorescent nanoparticles onto the polymer or polymer composite;
    (b) measuring diffusion of functionalized fluorescent nanoparticles or determining a concentration profile of functionalized fluorescent nanoparticles through a polymer matrix or polymer composite matrix; and
    (c) altering the temperature, pressure or stress on the polymer or polymer composite;
    wherein the measured diffusion or concentration profile of the fluorescent nanoparticles through the polymer or polymer composite is indicative of free volume, and wherein the measured concentration profile of the functionalized fluorescent nanoparticles throughout the polymer or polymer composite reveals nanoscopic changes occurring in the polymer or polymer composite.

2. The method of claim 1 wherein the solution of functionalized fluorescent nanoparticles is applied by spraying onto the polymer or polymer composite.

3. The method of claim 1, wherein the functionalized fluorescent nanoparticles are incorporated into the polymer or polymer composite.

4. The method of claim 1 wherein at least one of the fluorescent nanoparticles is functionalized to attach preferentially to at least one chemical component of the polymer matrix or polymer composite matrix.

5. The method of claim 4 wherein a second fluorescent nanoparticle is functionalized to attach preferentially to a second chemical component of the polymer matrix or polymer composite matrix, said second chemical component being different than the first chemical component.

6. A method for tracking changes in different components of a polymer composite comprising contacting a polymer composite with fluorescent nanoparticles wherein at least one of the fluorescent nanoparticles is functionalized to attach preferentially to at least one chemical component of the polymer matrix or polymer composite matrix, and wherein a second fluorescent nanoparticle is functionalized to attach preferentially to a second chemical component of the polymer matrix or polymer composite matrix, said second chemical component being different than the first chemical component and monitoring diffusion of the differently functionalized fluorescent nanoparticles through the polymer composite.

7. A method for monitoring or quantifying crack propagation and fatigue of a polymer or polymer composite comprising contacting the polymer or polymer composite with fluorescent nanoparticles functionalized with a molecule that recognizes a moiety at the damaged crack site and monitoring via fluorescence diffusion of the functionalized fluorescent nanoparticles through the polymer or polymer composite.

8. The method of claim 7 wherein the functionalized fluorescent nanoparticles are in a solution sprayed onto the polymer or polymer composite.

9. The method of claim 7 wherein the functionalized fluorescent nanoparticles are incorporated into the polymer or polymer composite.

10. A method for delivering a repair agent to a crack in a polymer or polymer composites comprising attaching a repair agent to a fluorescent nanoparticle functionalized with a molecule that recognizes a moiety at the damaged crack site and contacting the cracked polymer or polymer composite with the repair agent attached to the functionalized fluorescent nanoparticle so that the repair agent diffuses to damaged crack site.

11. The method of claim 10 wherein the repair agent comprises an adhesive agent or a cross-linking agent.

* * * * *